Figure 1A:
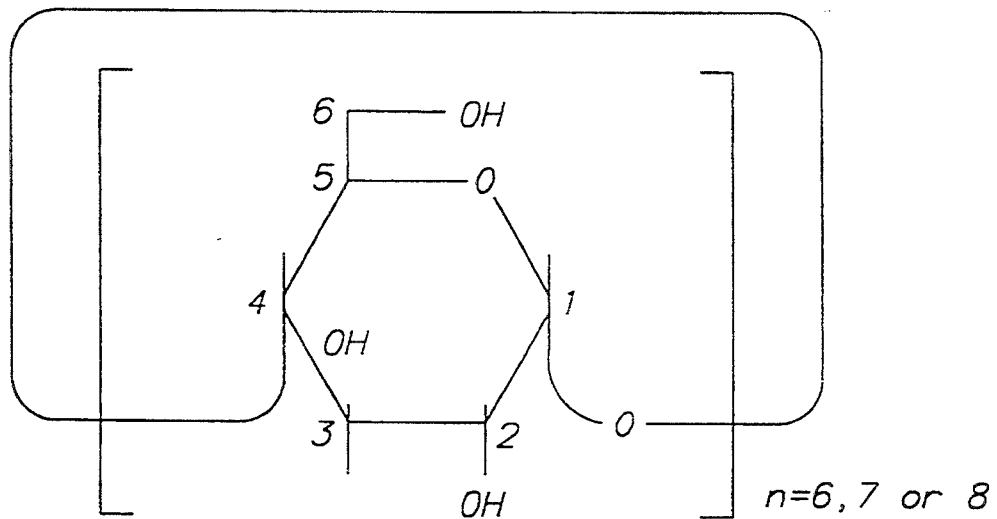

United States Patent [19]
Weisz et al.

[11] Patent Number: 5,441,944
[45] Date of Patent: * Aug. 15, 1995

[54] SUBSTITUTED CYCLODEXTRIN SULFATES AND THEIR USES AS GROWTH MODULATING AGENTS

[75] Inventors: Paul B. Weisz, State College; William R. Ewing, King of Prussia; Madeleine M. Joullie, Philadelphia, all of Pa.

[73] Assignee: The Trustees of the University of Pennsylvania, Philadelphia, Pa.

[ * ] Notice: The portion of the term of this patent subsequent to May 28, 2008 has been disclaimed.

[21] Appl. No.: 947,417

[22] Filed: Sep. 18, 1992

Related U.S. Application Data

[63] Continuation of Ser. No. 691,168, Apr. 24, 1991, abandoned, which is a continuation of Ser. No. 397,559, Apr. 23, 1989, abandoned.

[51] Int. Cl.$^6$ ............... A61K 31/70; C08B 37/02; C08B 37/16
[52] U.S. Cl. ............... 514/58; 514/908; 536/103
[58] Field of Search ............... 514/58, 908; 536/103

[56] References Cited

U.S. PATENT DOCUMENTS

| | | | |
|---|---|---|---|
| 2,923,704 | 2/1960 | Berger et al. | 536/103 |
| 3,420,788 | 1/1969 | Solms | 260/17.4 |
| 4,020,160 | 4/1977 | Bernstein et al. | 424/180 |
| 4,066,829 | 1/1978 | Nair et al. | 536/103 |
| 4,247,535 | 1/1981 | Lewis et al. | 424/180 |
| 4,258,180 | 3/1981 | Lewis et al. | 536/112 |
| 4,383,992 | 5/1983 | Lipari | 424/238 |
| 4,582,900 | 4/1986 | Brandt et al. | 536/103 |
| 4,596,795 | 6/1986 | Pitha | 514/58 |
| 4,727,064 | 2/1988 | Pitha | 514/58 |
| 4,764,604 | 8/1988 | Müller | 536/103 |
| 4,834,985 | 5/1989 | Elger et al. | 424/488 |
| 4,840,941 | 6/1989 | Ueno et al. | 514/59 |
| 4,877,774 | 10/1989 | Pitha et al. | 514/26 |
| 4,877,778 | 10/1989 | Carpenter et al. | 514/58 |
| 4,902,788 | 2/1990 | Zemel et al. | 536/1.1 |
| 5,019,562 | 5/1991 | Folkman et al. | 514/58 |

FOREIGN PATENT DOCUMENTS

| | | |
|---|---|---|
| 0121777 | 10/1984 | European Pat. Off. . |
| 0188821 | 7/1986 | European Pat. Off. . |
| 0193850 | 9/1986 | European Pat. Off. . |
| 0325199 | 7/1989 | European Pat. Off. . |
| 0447171 | 9/1991 | European Pat. Off. . |
| 50-36422 | 4/1975 | Japan . |
| 50-140476 | 11/1975 | Japan . |
| 62-123196 | 6/1987 | Japan . |
| 63-122701 | 5/1988 | Japan . |
| 1315401 | 12/1989 | Japan . |
| WO85/02767 | 7/1985 | WIPO . |
| WO89/06536 | 7/1989 | WIPO . |

OTHER PUBLICATIONS

Croft et al., *Tetrahedron*, vol. 39, pp. 1417–1474 (1983).
Nakashima et al., *Antimicrobial Agents and Chemotherapy*, pp. 1524–1528 (1987).
Uekama et al., *International Journal of Pharmaceutics*, vol. 10, pp. 1–15 (1982).
J. Pitha et al., *Journal of Pharmaceutical Sciences*, vol. 75(2), pp. 165–167 (1986).

(List continued on next page.)

*Primary Examiner*—Ronald W. Griffin
*Attorney, Agent, or Firm*—Duane, Morris & Heckscher

[57] ABSTRACT

The invention relates to highly water soluble substituted $\alpha$-, $\beta$- or $\gamma$-cyclodextrin sulfates associated with a physiologically acceptable cation. Pathological or otherwise undesirable cell or tissue growth in mammals, including humans, is inhibited by administering thereto (1) a water-soluble substituted cyclodextrin sulfate salt, together with (2) a growth-inhibiting organic compound. The growth-inhibiting compound (2) may be a steroid having no inhibiting effect in the absence of (1), or an organic compound which may be an active growth inhibitor, the action of which is potentiated by (1). The invention provides a method for inhibiting angiogenesis and controlling the growth of tumors as well as treating other diseases and pathological conditions associated with undesired cell or tissue growth, including angiogenesis.

18 Claims, 1 Drawing Sheet

OTHER PUBLICATIONS

Gimbrone et al., *J. Nat'l. Cancer Inst.*, vol. 52, pp. 413–426 (1973).

J. Folkman et al., *Science*, vol. 221, pp. 719–725 (1983).

Snow et al., *Human Pathology*, vol. 18, pp. 506–510 (1987).

*Chemical Abstracts* 83:79544a (1975).

Fenyvesi et al., *Chem. Pharm. Bull.*, vol. 32(2), pp. 665–669 (1984).

Fenyvesi et al., *Chem. Pharm. Bull.*, vol. 32(2), pp. 670–677 (1984).

Komiyama et al., *Polymer Journal*, vol. 18(4), pp. 375–377 (1986).

*Chemical Abstracts*, 96:218351U (1982).

Herrmann, H. C., *Abstracts of Papers*, National Meeting of the American Heart Association, Ahaheim, Calif.; Nov. 11–14, 1991.

Yamamoto et al., *International Journal of Pharmaceutics*, vol. 49, pp. 163–171 (1989).

J. Folkman et al., *Science*, vol. 235, pp. 442–447 (1987).

J. Folkman et al., *Cancer Research*, vol. 46, pp. 467–473 (1986).

Shubik et al., *J. Nat'l. Cancer Inst.*, vol. 57, pp. 769–774 (1976).

Gross et al., *Proc. Nat'l. Acad. Sci. USA*, vol. 78, pp. 1176–1180 (1981).

R. Crum et al., *Science*, vol. 230, pp. 1375–1378 (1985).

J. Folkman et al., *Annals of Surgery*, vol. 206, pp. 374–383 (1987).

SUBSTITUTED CYCLODEXTRIN SULFATES AND THEIR USES AS GROWTH MODULATING AGENTS

This is a continuation of application Ser. No. 07/691,168, filed Apr. 24, 1991, now abandoned, which is a continuation of application Ser. No. 07/397,559, filed Aug. 23, 1989, now abandoned.

TABLE OF CONTENTS

1. Field of the Invention
2. Background of the Invention
   2.1. Heparin and Inhibition of Angiogenesis
   2.2. Cyclodextrins
3. Summary of the Invention
4. Brief Description of the Figures
5. Detailed Description of the Invention
   5.1. Water-Soluble Substituted Cyclodextrin Sulfates
   5.2. Steroids and Non-Steroidal Organic Compounds
   5.3. Applications and Methods of Use
6. Examples
   6.1. Synthesis of n-Tetrapropoxy-$\beta$-Cyclodextrin Sulfate
   6.2. Analysis of n-Tetrapropoxy-$\beta$-Cyclodextrin Sulfate
      6.2.1. Conductivity Measurements
      6.2.2. Dye Staining Analysis For High Density Sulfate Saccharides
      6.2.3. n-Tetrapropoxy-$\beta$-Cyclodextrin Sulfate Along With Hydrocortisone Inhibits Angiogenesis

1. Field of the Invention

This invention relates to substituted cyclodextrin sulfates associated with a physiologically acceptable cation. The present invention is also directed to a growth-inhibiting composition comprising a highly water soluble substituted cyclodextrin sulfate associated with a physiologically acceptable cation and a latent or active growth-inhibiting compound, and to the use of this composition to inhibit undesired or pathological growth, including angiogenesis which is associated with, inter alia, the growth of malignant tumors.

2. Background of the Invention

2.1. Heparin and inhibition of angiogenesis

Angiogenesis, the induction of growth of new capillary blood vessels, is important in normal processes such as development of the embryo, formation of the corpus luteum and healing of wounds. It is also an important component in pathological processes such as chronic inflammation, certain immune responses, and neoplasia. It is now accepted that angiogenesis is induced by most malignant tumors and that it is necessary for their continued growth and survival. It is also recognized that angiogenesis is a major component of a number of ophthamological pathologies including such as diabetic retinopathy, retrolental fibroplasia and neovascular glaucoma. Additionally, angiogenesis is now recognized as a major component in other non-neoplastic pathological conditions including rheumatoid arthritis, in which abnormal capillary growth can destroy joint cartilage; hemanogiomas, in which abnormal capillary proliferation appears in newborns and can persist for up to 2 years; angiofibromas which develop in the nasopharynx; and psoriasis, in which excessive proliferation and shedding may be dependent on abnormal capillary growth in the dermis [see Folkman and Klagsbrun, Science 235:442 (1987)].

It has been previously discovered that heparin (or heparin fragments) and cortisone will co-act together to inhibit angiogenesis. This is described in U.S. patent application Ser. No. 641,305 filed Aug. 16, 1984, the contents of which are incorporated herein by reference. When administered together to mice with certain kinds of tumors, this combination can inhibit the generation of essential capillary vessels that support tumor growth, and can cause the collapse of the blood supply which supports the tumors. A review of the history of this discovery and of related subject matter is contained in the publication "How is Blood Vessel Growth Regulated in Normal and Neoplastic Tissue?" (G.H.A. Clowes Memorial Award Lecture), Judah Folkman, Cancer Research, 46:467 (1986) the contents of which are incorporated herein by reference for background.

Cortisone is an anti-inflammatory agent that by itself does not have the ability to inhibit capillary growth. It has been reported in Shubik et al., J. Nat'l Cancer Inst. 57:769 (1976) that 6 $\alpha$-methyl prednisolone partially suppressed tumor angiogenesis in hamster cheek pouches under certain conditions, but tumor growth was not stopped. Many other publications have reported continued growth of tumors even in the presence of large amounts of cortisone. It has also been reported [Gross et al., Proc. Nat'l. Acad. Sci. USA 78:176 (1981)] that medroxyprogestrone, dexamethasone and to a lesser extent cortisone, inhibited tumor angiogenesis in rabbit corneas, while estradiol and testosterone were ineffective.

Aside from cortisone, certain other steroids are now known to successfully suppress angiogenesis when administered together with heparin or certain heparin fragments. The effective steroids have been referred to as "heparin-dependent" because heparin was (until now) unique in its effect. The findings and the character of desirable angiostatic steroids has been discussed in "A New Class of Steroids Inhibits Angiogenesis in the Presence of Heparin or a Heparin Fragment" R. Crum, S. Szabo and J. Folkman, Science 230:1375 (1985); and in "Angiostatic Steroids" J. Folkman and D. E. Ingber, Annals of Surgery, 206:374 (1987) incorporated herein by reference for background purposes.

Heparin, a mucopolysaccharide, is a constituent of various tissues, especially liver and lung, and mast cells in several mammalian species. Chemically, it has been described as an $\alpha$, $\beta$ glycosidically linked sulfated copolymer of D-glucosamine and D-glucuronic acid. However, although heparin has been used clinically as an anticoagulant for half a century, both the exact structure of heparin and the precise nature by which it acts in blood anticoagulation have not been discovered. Much of the difficulty in determining the structure of heparin results from its complexity and the fact that it is not a homogeneous, well-defined substance. Heparin is polydisperse with a molecular weight range from about 5,000 to 40,000. Within a given chain, there are also structural variations such as the varying degrees of sulfation, N-acetylation and C-5 epimerization in the uronic acid residue.

A major disadvantage in the use of heparin with a steroid to inhibit angiogenesis results from the fact that heparins manufactured by different processes and different companies revealed quite different antiangiogenic activities despite similar anticoagulant activities. The precise composition of commercial heparin apparently varies depending on its source and method of manufacture. While some heparins may be combined with cortisone to inhibit angiogenesis, other heparins are not effective as such. In fact, some heparins in order to be effective may be required in such high doses that administration may cause problems due to the anticoagulant activity of heparin. A second disadvantage is that while heparins apparently can inhibit the growth of responsive tumors when administered in the proper dose range and proper ratio to steroid, and even, promote regression at somewhat higher doses and ratios; heparins can also cause resumption of rapid tumor growth when administered at even higher dose levels and ratios to steroid. The apparent presence of both positive and negative regulators of angiogenesis in heparin may create problems in properly administering the drug. An additional disadvantage derives from the anticoagulant activity of heparin, restricting its use to low dosage levels or to oral administration in order to avoid bleeding. Finally because heparin cannot penetrate the corneal membrane, it cannot be topically applied to the exterior of the cornea for its desired antiangiogenic activity.

2.2. Cyclodextrins

Cyclodextrins (hereinafter referred to for convenience as CD or CDs for the singular and the plural, respectively) are cyclic oligosaccharides consisting of at least six glucopyranose units. Although CDs with up to twelve glucopyranose units are known, only the first three homologs have been studied extensively. These compounds have the simple, well-defined chemical structure shown in FIG. I(A). The common designations of the lower molecular weight $\alpha$-, $\beta$- and $\gamma$-CDs are used throughout this specification and will refer to the chemical structure shown in FIG. 1(A) wherein n=6, 7, or 8 glucopyranose units, respectively. The initial discovery of the CDs as degradation products of starch was made at about the turn of the century, and Schardinger showed that these compounds could be prepared by the action of *Bacillus macerans* amylase upon starch. In older literature, the compounds are often referred to as Schardinger dextrins. They are also sometimes called cycloamyloses.

Figure 1B:
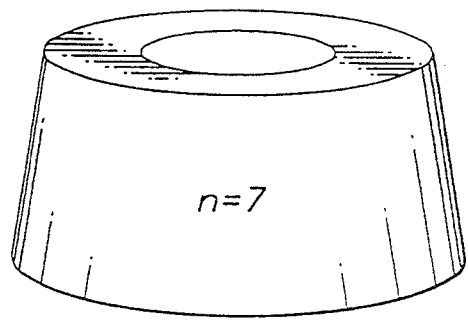

Topographically, the CDs may be represented as a torus, as shown in FIG. 1(B), the upper rim of which is lined with primary —CH$_2$OH groups, and the lower rim with secondary hydroxyl groups. Coaxially aligned with the torus is a channel-like cavity of about 5, 6 or 7.5 A.U. diameter for the $\alpha$-, $\beta$-, and $\gamma$-CDs, respectively. These cavities make the cyclodextrins capable of forming inclusion compounds with hydrophobic guest molecules of suitable diameters.

A reasonably large number of CD derivatives have been prepared and described in the literature. In general, these chemically modified CDs are formed by reaction of the primary or secondary hydroxyl groups attached to carbons 2, 3 or 6 [FIG. 1(A)], without disturbing the $\alpha$ (1→4) hemiacetal linkages. A review of such preparations is given in "Tetrahedron Report Number 147, Synthesis of Chemically Modified Cyclodextrins", A. P. Croft and R. A. Bartsch, Tetrahedron 39(9):1417–1474 (1983), incorporated herein by reference for background (hereinafter referred to as "Tetrahedron Report No. 147").

In particular, $\alpha$-, $\beta$-, and $\gamma$-CD sulfates (Na salt) are shown as Compound Nos. 207, 208, and 209 in Tetrahedron Report No. 147, (supra) Table 26, p.1456. U.S. Pat. No. 2,923,704 to Berger describes the preparation of cycloamylose sulfates. U.S. Pat. No. 4,020,160 to Berstein et al. and U.S. Pat. Nos. 4,247,535 and 4,258,180 to Lewis et al. disclose the use of modified cyclodextrin sulfates as complement inhibitors. U.S. Pat. No. 4,383,992 to Lipari describes the preparation of a water-soluble inclusion compound of a steroid and unmodified $\beta$-cyclodextrin. U.S. Pat. No. 4,596,795 to Pitha discloses the administration (by the sublingual or buccal route) of sex hormones, particularly testosterone, progesterone and estradiol in the form of their inclusion compounds with hydroxypropyl-$\beta$-CD or poly-$\beta$-CD. None of the foregoing references are believed to show or make obvious applicants' invention as described and claimed herein.

3. SUMMARY OF THE INVENTION

This invention is directed to highly water soluble substituted cyclodextrin sulfates associated with a physiologically acceptable cation. The substituents include but are not limited to alkyl groups, esters, ethers, thioesters, thioethers, carboxylic acids or other groups which convey hydrophilic activity by way of polar or hydrogen bonding constituents. Substitution may occur at all or some of the hydroxyl groups.

This invention also provides a composition for inhibiting undesired or pathological cell or tissue growth (including angiogenesis) in mammals, including humans, said composition comprising (1) a very water-soluble substituted $\alpha$-, $\beta$- or $\gamma$-cyclodextrin sulfate associated with a physiologically acceptable cation in combination with (2) a latent growth-inhibiting steroid or a non-steroidal growth-inhibiting organic compound.

This invention further provides a method of inhibiting undesired or pathological cell or tissue growth (including angiogenesis) in mammals, including humans, comprising administering thereto a growth-inhibiting amount of active agents consisting essentially of (1) a very water-soluble substituted $\alpha$-, $\beta$- or $\gamma$-cyclodextrin sulfate associated with a physiologically acceptable cation in combination with (2) a latent growth-inhibiting steroid or a non-steroidal growth-inhibiting organic compound. The method of the invention can be accomplished either by mixing the two active agents and administering the combination via a single route or, alternatively, by administering each of the active agents separately and permitting the combination to form in vivo. According to the alternative mode, the two active agents can be administered separately via the same or different routes, so long as both agents are thus allowed to be present simultaneously in combination in vivo.

This invention further provides a method of inhibiting angiogenesis in mammals, including humans, comprising administering thereto an angiogenesis-inhibiting amount of a composition comprising active agents consisting essentially of (1) a very water-soluble substituted $\alpha$-, $\beta$- or $\gamma$-cyclodextrin sulfate associated with a physiologically acceptable cation in combination with (2) at least one angiogenesis inhibitor selected from the group consisting of a latent growth-inhibiting steroid and a non-steroidal growth-inhibiting organic compound, said derivative being characterized by a solubility in distilled water of at least about 20 grams per 100 milliliters of water at 0° C.

This invention further provides a method of inhibiting the pathological growth of smooth muscle cells in mammals, including humans, in need of such treatment, which method comprises administering thereto a growth-inhibiting amount of a composition comprising a very water-soluble substituted cyclodextrin sulfate associated with a non-toxic physiologically acceptable cation.

4. BRIEF DESCRIPTION OF THE FIGURES

The present invention may be more fully understood by reference to the following detailed description of the invention, examples of specific embodiments of the invention and appended figures in which:

FIG. 1(A and B) is a schematic representation of: (A) the chemical structure of α-, β- and γ-cyclodextrins; and (B) of the three-dimensional shape of these cyclodextrins.

5. DETAILED DESCRIPTION OF THE INVENTION

The present invention is directed to highly water soluble substituted cyclodextrin sulfates associated with a physiologically acceptable cation. An example of one such highly water soluble substituted CD sulfate which is described in Section 6, infra.

The present invention also relates to a composition comprising a highly water soluble substituted cyclodextrin sulfate associated with a physiologically acceptable cation in combination with asteroid or a non-steroidal compound that inhibits growth in the absence of exogenous heparin which effectively inhibit undesired cell or tissue growth, including angiogenesis, and for treating tumors in mammals. In particular and as will be described in the example section herein, n-tetrapropoxy β-cyclodextrin sulfate was found to be very effective. These findings set aside the notion that heparin is unique in its role in suppressing angiogenesis when combined with a suitable steroid.

To clearly distinguish the steroids (which in the absence of exogenous heparin, have no inherent antiangiogenic activity) from such non-steroidal growth-inhibitory compounds, the qualifying phrase "latent growth-inhibiting" is used herein. The adjective "non-steroidal" as used herein means a compound in which carbon ring structure characteristic of a sterol is absent.

5.1. Water-soluble Substituted Cyclodextrin Sulfates

Highly water-soluble substituted cyclodextrin (CD) sulfates associated with a physiologically acceptable cation are useful for inhibiting undesired growth according to the present invention. These compounds have not been disclosed in the prior art. Suitable highly water-soluble substituted α-, β- and γ sulfates CD include substituted α, β and γ sulfates CD having substituents including but not limited to alkyl substituents such as methyl, ethyl, n-propyl, isopropyl etc., as well as those in which a number of hydroxyl groups are replaced by other groups so as to increase the hydrophilic activity of the substituted CD sulfate. Such groups include esters (e.g. alkyl), ethers (e.g. alkoxy), thioesters (e.g. alkyl), thioethers (e.g. alkyl), carboxylic acids (e.g. alkyl) or other groups which convey hydrophilic activity by way of polar or hydrogen bonding constituents. Substitution may occur at some or all of the hydroxyl groups. The substituted CD sulfates may be prepared using methods known to those skilled in the art.

The substituted CD sulfates useful in the present invention are highly hydrophilic and therefore very water soluble, with a solubility of at least 20 gm/100 ml in water at 0° C. Without wishing to be bound by theory, we believe that a highly hydrophilic character is important to allow interaction with cellular surfaces. We also believe a very high water solubility of the derivative is an important factor which cooperatively interacts with the inherent complexing ability of the CD structure to provide effective inhibition of angiogenesis with an exogenous steroid, as provided by this invention. We believe that the hydrophilic activity is roughly indicated by the affinity to water, as measured by water solubility. It is important to measure the same at 0° C. since at higher temperatures the most suitable derivatives have solubilities so high that it is difficult to obtain meaningful measurements.

The α-, β- and γ substituted CD sulfate salts are all usable in the presently claimed invention. Substituted β-CD sulfate salts are preferred. Various degrees of sulfation per glucose unit can be employed, such as an average of one sulfate group per two glucose units or two sulfate groups per glucose unit. Cyclodextrins having about two sulfate groups per glucose unit are preferred. Especially preferred is substituted β-CD-TDS which has an average of two sulfate groups per glucose unit.

5.2. Steroids and Non-steroidal Organic Compounds

Among the latent growth-inhibiting steroids which are effective and can be utilized in the presently claimed invention are the following:

17 alpha, 21-dihydroxy-4-pregene-3,11,20-trione and its 21-acetate (or cortisone);

11 alpha, 17,21-trihydroxypregn-4-ene-3,20-dione (or 11 alpha hydrocortisone);

11 beta, 17 alpha, 21-trihydroxypregn-4-ene-3,20-dione (or hydrocortisone);

17 alpha, 21-dihydroxypregna-4,9(11)-diene-3,20-dione;

15 alpha, 17 alpha, 21-trihydroxy-4-pregnene-3,20-dione;

16 alpha, 17 alpha, 21-trihydroxy-6 alpha-methylpregn-4-ene-3,20-dione-21-acetate-16,17 cyclic ketal of acetone;

6 alpha-fluoro-17 alpha, 21-dihydroxy-16 beta-methylpregna-4,9(11)-diene-3,20-dione;

6 alpha-fluoro-18 alpha,21-dihydroxy-16 beta-methylpregna-4,9(11)-diene-3,20-dione-17,21-diacetate;

6 beta, 17 alpha, 21-trihydroxypregn-4-ene-3,20-dione;

17 alpha, 21-dihydroxypregn-4-ene-3,20-dione-21-acetate;

17 alpha, 21-dihydroxypregn-4-ene-3,20-dione (or Cortexolone);

9 beta, 11 beta-epoxy-17 alpha, 21-dihydroxy-2 alpha-methylpregn-4-ene-3,20-dione-21-acetate;

17 alpha, 21-dihydroxy-16 alpha-methylpregn-4-ene-3,20-dione;

9 alpha, 11 beta-dichloro-17 alpha, 21-dihydroxypregn-4-ene-3,20-dione-21-acetate 17 alpha, 21-dihydroxy-6 alpha, 16 alpha-dimethylpregn-4-ene-3,20-dione-21-acetate;

17 alpha, 21-dihydroxy-16 alpha-methylpregna-4,9(11)-diene-3,20-dione-21-acetate;

17 alpha, 21-dihydroxy-16 beta-methylpregna-4,9(11)-diene-3,20-dione-21-benzoate;

6 alpha-fluoro-17 alpha, 21-dihydroxy-16 beta-methylpregna-4,9(11)-diene-3,20-dione-17-acetate-21-benzoate;

17 alpha, 21-dihydroxy-16 beta-methylpregna-1,4,9(11)-triene-3,20-dione-17-succinate sodium monohydrate;

9 alpha-fluoro-11 beta, 16 alpha, 17 alpha, 21-tetrahydroxy-pregn-4-ene-3,20-dione-16,21-diacetate;

17 alpha, 21-dihydroxy-16 alpha-methylpregna-1,4,9(11)-triene-3,20-dione-21-succinate sodium monohydrate;

6 alpha-fluoro-17 alpha, 21-dihydroxy-16 beta-methyl-pregna-1,4,9(11)-triene-3,20-dione-21-succinate sodium;
desoxycorticosterone;
testosterone;
estrone; and
tetrahydro S.

More preferred are those latent growth-inhibiting steroids which lack glucocorticoid and mineralo-corticoid activity, since such activity is an undesired effect and limits the dose size or extent of use of the steroid for the purpose of the present invention. Among such more preferred steroids are 11 alpha, 17,21-trihydroxypregn-4-ene-3,20-dione (or 11 alpha-hydrocortisone), 17 alpha, 21-dihydroxypregn-4-ene-3,20-dione (11-desoxycortisol or cortexolone), and 17 alpha, 21-dihydroxypregna-4,9(11)-diene-3,20-dione.

The term "cortisone" and "hydrocortisone" and 11-α isomer of hydrocortisone as used in the present specification and claims are intended to include both the steroids themselves and their derivatives and structural variants.

None of the latent growth-inhibiting steroids themselves effectively inhibits angiogenesis nor causes regression of tumors in the absence of a highly water-soluble substituted cyclodextrin sulfate associated with a physiologically acceptable cation of the present invention.

As taught by the present invention, the growth-inhibitory activity of non-steroidal organic compounds is potentiated by combination with a water-soluble substituted cyclodextrin sulfate associated with a physiologically acceptable cation. Among the non-steroidal growth-inhibiting organic compounds which are effective and can be utilized in the presently claimed invention are the following: proline analogs such as L-2 azetidinecarboxylic, cis-hydroxyproline, and 3,4-dihydroproline and trans-retinoic acid.

Additionally, any non-steroidal organic compound which in combination with a substituted cyclodextrin sulfate associated with a physiologically acceptable cation demonstrates growth inhibiting activity in either of the bioassays described below can be utilized in the methods of the presently claimed invention.

Several bioassays have been developed to estimate the angiogenic-inhibiting potency, if any, of a substance. The rabbit cornea is the basis of one of these methods. The cornea is avascular. A small pocket can be made in it and a tumor implant can be inserted while the rabbit is anesthetized. The tumor is separated from the vascular bed of the host. New capillary blood vessels will grow in a linear manner toward the tumor, and the rate of vessel growth can be measured. [For a more detailed description of this assay, see, Gimbrone et al., J. Nat'l Cancer Inst. 52:413 (1973) incorporated herein by reference].

A more economic bioassay makes use of the chorioallantoic membrane of the chick embryo. This test will for convenience be referred to hereinafter as the "CAM assay". For a more detailed description of the CAM assay, see Folkman et al., Science 221:719 (1983), incorporated herein by reference. A typical CAM assay, such as used for the evaluations in the example in Section 6, infra, employs 16 eggs per experiment. A 2 mm diameter disk of methylcellulose containing the test substance is applied to the chorioallantoic membrane of a 6-day chick embryo, cultured in a Petri dish, in a humidified incubator with 3% carbon dioxide. Two days later (8-day embryo), the membrane is examined under a stereomicroscope at six- to ten-fold magnification. Inhibition of angiogenesis by the test substance is evidenced by the development of an avascular zone around the methylcellulose disc. An avascular zone of 4 mm is graded as (++) and an avascular zone of 2 mm is graded at (+). The potency of the inhibition at the 2 mm and 4 mm zone(s) are expressed as the percentage of the total number of eggs (usually 16) in the test that were rated (++) or (+), i.e., the % of "successes". A rating of zero % reflects absence of inhibition of the test substance under the test conditions.

The sustained release methylcellulose discs are prepared by dispersing appropriate amount(s) of the test substance of substances in an 0.45% aqueous solution of methylcellulose, and depositing 10 microliter aliquots of the resulting solution in a Teflon mold, followed by air drying for about one hour in a laminar flow hood.

A very advantageous feature of the CAM assay is the very high sensitivity of the chick embryo to toxic substances. Moreover, the lack of toxicity of a substance in the CAM assay has been correlated with lack of toxicity of such substance when administered to other animals.

5.3. Applications and Methods of Use

The composition of the present invention is useful for inhibiting undesired cell and tissue growth, including angiogenesis. Of course, the composition of the present invention comprising a water soluble substituted α-, β- or γ-CD sulfate associated with a physiologically acceptable cation and asteroid is to be administered to mammals including humans in need of such treatment. For example, mammals with tumors are in need of treatment with the composition of the present invention. While not completely understood, it is believed that treatment with the composition of the present invention inhibits the creation of new capillaries necessary for tumor growth. This results in the tumor having an insufficient supply of nutrients essential for its growth or even for its vitality. Thus, tumors in mammals including humans, when treated in accordance with the present invention, do not grow and may even lose their vitality and die. Among the tumors contemplated as responsive to the composition and methods of this invention are Reticulum Cell Sarcoma, Lewis Lung Carcinoma, B-16 Melanoma, and Bladder Carcinoma, etc.

Neither mature non-growing blood vessels nor mature non-growing vascular tissue appear to be affected by the treatment with the composition of the present invention. Inhibition of angiogenesis in accordance with the present invention, in addition to its effect upon tumor regression and metastasis in tumor-bearing animals, may be effective in treating a number of other ailments.

The present invention further provides a method for treatment of a number of other non-tumorous disorders which are characterized by pathological cell or tissue growth, including angiogenesis. Thus the invention provides a method for treatment of mammals, including humans, afflicted with a number of non-neoplastic pathological conditions including rheumatoid arthritis, in which abnormal capillary growth can destroy joint cartilage; hemanogiomas, in which abnormal capillary proliferation appears in newborns and can persist for up to 2 years; angiofibromas which develop in the nasopharynx; psoriasis, in which excessive proliferation and shedding may be dependent on abnormal capillary growth in the dermis. Additionally, the present invention provides a method for treatment of a number of ophthalmological pathologies which are associated with undesired angiogenesis, including diabetic retinopathy, retrolental fibroplasia and neovascular glaucoma.

The present invention further provides a method for inhibiting undesired smooth muscle cell development often observed following angioplasty or treatment to remove atherosclerotic plaques which occlude blood vessels.

According to one embodiment of the method of the present invention, the active agents are mixed together prior to administration so that the steroid compound or non-steroidal growth-inhibiting compound is administered in combination with the water-soluble substituted cyclodextrin sulfate associated with a physiologically acceptable cation. After the mixture is prepared, it may be administered orally or parenterally including, inter alia, topical application, intravenous, intra-arterial or subcutaneous injection, and including absorption as well as injection and introduction into body apertures or orifices.

Cortisone and its physiologically accepted non-toxic derivatives, such as the acetates, as well as many other steroids useful in the present invention, are only slightly soluble in water. However, when combined with the water-soluble substituted cyclodextrin sulfates of the invention, the resulting complexes have increased water solubility. Accordingly, the composition of the present invention can easily be administered.

According to an alternate embodiment of the method of the invention, the active agents are each administered separately and the combination of the two agents forms in vivo. In this embodiment, the two active agents can be introduced separately either via the same or different routes of administration, so long as both agents are thus present simultaneously in vivo, permitting a complex mixture of the two active agents to form.

Dosages employed are limited only by the well-known limits of the administration of drugs individually for their usual effects, in the case of cortisone, hydrocortisone, or 11-α isomer. Simple testing, for example by the procedure of Example 3 in U.S. patent application Ser. No. 641,305, filed Aug. 16, 1984, suffices to determine effectiveness and optimum dose. The procedure of Example 3 is incorporated herein by reference.

The dose amount required to bring about arrest of tumor growth or regression of tumors varies depending upon the identity of the tumor, as does the length of time required to bring about arrest or regression of tumors. Tumor size at the beginning of treatment also affects the length of time for complete regression. Because administration of cortisone, with or without the substituted β-cyclodextrin sulfate (Na), for example, may result in pulmonary infection after a number of days, it may be desirable to administer a suitable antibiotic as a prophylactic during treatment in accordance with the present invention. Such antibiotics can be mixed with the water-soluble substituted cyclodextrin sulfate and the steroid or non-steroidal growth-inhibiting agents of the invention and administered as a mixture or, alternatively, the antibiotics can be administered alone contemporaneously with the water-soluble substituted cyclodextrin sulfates and growth-inhibiting agents of the invention either by the same or a different route of administration.

The effective compositions of this invention are best administered in a suitable carrier, which must be non-toxic and physiologically acceptable, such as water or normal saline solution. Compositions containing mixtures of the active agents or each of the active agents alone, either dry or in a suitable carrier, can be employed.

6. EXAMPLES

The following examples are provided to illustrate this invention. However, they are not to be construed as limiting the scope of the invention, which scope is determined by this entire specification including the appended claims. All amounts and proportions shown are by weight unless explicitly stated to be otherwise.

6.1. Synthesis of n-tetrapropoxy-β-cyclodextrin Sulfate 1.0 gram of n-tetrapropoxy-β-cyclodextrin (American Maize Processing Company, Hammond, Ind.) was dissolved in 15 ml of dimethylformamide (DMF). To the solution, at 60° C. was added 2 g of $(CH_3)_3$—$NSO_3$. The reaction was allowed to proceed for 16 hours. After cooling to room temperature, 15 ml ethanol was added, and the mixture filtered. The residue was dissolved in 30 ml of 30% sodium acetate (aq.). After stirring 4 hours, 3:1 solution of ethanol/ethyl ether was added and a white precipitate was separated, redissolved in 30 ml of water and reprecipitated with the 3:1 ethanol/ethyl ether mixture. The resulting precipitate product was collected and dried over $P_2O_5$.

6.2. Analysis of n-tetrapropoxy-β-cyclodextrin Sulfate n-Tetrapropoxy-β-cyclodextrin sulfate was analyzed by conductivity measurements and by measuring its affinity to the cationic dye, Alcian Blue. Methods and results are described below.

6.2.1. Conductivity Measurements

Conductivity is an accepted method for measuring the degree of ionic substitution and can be used to evidence the addition of a charged group, such as sulfate to a compound. Substituted cyclodextrins do not generate or add electrical conductivity in water. Results of conducting measurements obtained in deionized water having a background conductivity of 2.5 $(\pm 0.2) \times 10^6$ mho/cm are shown in Table I.

TABLE I

| Compound | Conductivity ($10^{-4}$ mho/cm per mg/ml) |
|---|---|
| β-cyclodextrin | immeasurable |
| n-tetrapropoxy β-cyclodextrin | immeasurable |
| n-tetrapropoxy β-cyclodextrin sulfate | 4.5 |
| β-cyclodextrin tetradecasulfate* | 4.6 |

*average of 2 samples

The results indicate that n-tetrapropoxy-β-cyclodextrin sulfate was indeed sulfated and that the degree of ionization was as great as that of β-cyclodextrin tetradecasulfate.

6.2.2. Dye Staining Analysis for High Sulfate Density Saccharides

Complexing behavior of sugars with certain polycationic dyes, including Alcian Blue, is known to be useful as an indicator of high density sulfate groups on saccharides, including those having other polar substituents, as demonstrated for a variety of glycosaminoglycans. Such complexing behavior has been utilized in histology, for selective staining to indicate high sulfur natural saccharides such as heparin (Snow et al., 1987, Human Pathology 18:506–510 and Dorling, 1969, Med. Lab. Techn. 26:124–130).

The following procedure was used to detect the presence of high density sulfate groups. An alumina TLC plate (Analtech, Newark, Del.) was spotted with a drop (1 µl) of a sample (0.8 mg/ml) to be tested. The spot or spots were dried for 10 minutes at about 60° C. Aqueous solution of 0.5 mg/ml of Alcian Blue (8GX, Aldrich), buffered with 0.25M acetate buffer at 5.6 pH is allowed to rise along the plate up to and past the test spot. The presence of high sulfate density sugar was revealed by blue staining of part of the spot, and a trailing "white shadow" of solution (from which dye was removed). A comparison of samples as in Table I, supra, reveals that only the sulfated propoxy cyclodextrin and the 14-sulfate containing cyclodextrin generate an Alcian Blue stain.

6.3.3. n-Tetrapropoxy-β-Cyclodextrin Sulfate Along with Hydrocortisone Inhibits Angiogenesis The angiogenesis inhibiting ability of n-propoxy-β-cyclodextrin sulfate was determined using a CAM assay (as described by Loebman et al. (1983, Science 221:719–725). Specifically, 25 µg of n-tetrapropoxy-β-cyclodextrin sulfate (solubility 37 gm/100 ml H$_2$O at 0° C.) and 50–60 µg of hydrocortisone in 10 µl of 0.45% methylcellulose in water was implanted on day 6 chick chorioallantoic membranes. The embryos were examined 48 hours later and the % of avascular zones was determined as described in Section 5.2, supra. It was found that n-tetrapropoxy-β-cyclodextrin sulfate plus hydrocortisone produced 37% avascular zones and was therefore an effective inhibitor of angiogenesis.

The invention described and claimed herein is not to be limited in scope by the specific embodiments herein disclosed, since these embodiments are intended as illustrations of several aspects of the invention. Any equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

What is claimed is:

1. A composition comprising (1) n-tetrapropoxy-β-cyclodextrin sulfate associated with a physiologically acceptable cation in combination with (2) a therapeutically effective amount of a therapeutic agent.

2. A composition for inhibiting undesired or pathological cell or tissue growth in mammals comprising (1) n-tetrapropoxy-β-cyclodextrin sulfate associated with physiologically acceptable cation in combination with (2) a latent growth-inhibiting steroid or a non-steroidal growth-inhibiting organic compound, in which the n-tetrapropoxy-β-cyclodextrin sulfate has a solubility at 0° C. in distilled water of at least about 20 gm/100 ml of water.

3. The composition according to claim 2, in which the steroid is 17-alpha, 21-hydroxy and 3,20-dione and has in the 16-position hydrogen, hydroxy or a methyl group and non-toxic, physiologically acceptable carboxylates, acetal, ketals and phosphates thereof.

4. The composition according to claim 2, in which the steroid is cortisone, hydrocortisone or cortexolone.

5. The composition according to claim 2, in which the non-steroidal growth-inhibiting organic compound is L-2-azetidinecarboxylic acid.

6. A method for inhibiting cell or tissue growth in mammals comprising administering to a mammal a growth-inhibiting amount of active agents consisting essentially of (1) n-tetrapropoxy-β-cyclodextrin sulfate associated with a physiologically acceptable cation in combination with (2) a latent growth-inhibiting steroid or non-steroidal growth-inhibiting organic compound, in which the n-tetrapropoxy-β-cyclodextrin sulfate has a solubility at 0° C. in distilled water of at least about 20 gm/100 ml of water.

7. The method of claim 6 wherein the active agents are mixed together prior to the administration.

8. The method of claim 6 wherein the active agents are administered separately, thereby forming the combination in vivo.

9. The method of claim 8 wherein the active agents are administered by the same or different route.

10. A method for inhibiting angiogenesis in mammals comprising administering to a mammal an angiogenesis-inhibiting amount of active agents consisting essentially of (1) n-tetrapropoxy-β-cyclodextrin sulfate associated with a physiologically acceptable cation in combination with (2) a latent growth-inhibiting steroid or non-steroidal growth-inhibiting organic compound, the n-tetrapropoxy-β-cyclodextrin sulfate having a solubility at 0° C. in distilled water of at least about 20 gm/100 ml of water.

11. The method according to claim 10, in which the steroid is 17-alpha, 21-hydroxy and 3,20-dione and has in the 16-position hydrogen, hydroxy or a methyl group and non-toxic, physiologically acceptable carboxylates, acetal, ketals and phosphates thereof.

12. The method according to claim 10, in which the steroid is cortisone, hydrocortisone or cortexolone.

13. The method according to claim 10, in which the non-steroidal growth-inhibiting organic compound is L-2-azetidinecarboxylic acid.

14. The method of claim 10 wherein the active agents are mixed together prior to the administration.

15. The method of claim 10 wherein the active agents are administered separately, thereby forming the combination in vivo.

16. The method of claim 15 wherein the active agents are administered by the same or different route.

17. A method for inhibiting the pathological growth of smooth muscle cells in mammals comprising administering to a mammal, a growth-inhibiting amount of n-tetrapropoxy-β-cyclodextrin sulfate associated with a physiologically acceptable cation, the n-tetrapropoxy-β-cyclodextrin sulfate having a solubility at 0° C. in distilled water of at least about 20 gm/100 ml of water.

18. The method according to claim 17, further comprising administering an amount of a latent growth-inhibiting steroid or a non-steroidal growth-inhibiting organic compound.

* * * * *